United States Patent

Fujii et al.

[11] Patent Number: 5,977,410
[45] Date of Patent: Nov. 2, 1999

[54] N-[(FLUOROALKOXY) PHENOXYALKYL] BENZAMIDE COMPOUNDS, INTERMEDIATES THEREOF, PROCESS FOR PRODUCING THE SAME, AND AGRICULTURAL AND HORTICULTURAL PESTICIDES

[75] Inventors: Katsutoshi Fujii; Koji Hatano; Shoji Shikita; Tatsumi Tanaka, all of Ube, Japan

[73] Assignee: Ube Industries, Ltd., Tokyo, Japan

[21] Appl. No.: 09/051,897

[22] PCT Filed: Oct. 24, 1996

[86] PCT No.: PCT/JP96/03090

§ 371 Date: Apr. 16, 1998

§ 102(e) Date: Apr. 16, 1998

[87] PCT Pub. No.: WO97/15551

PCT Pub. Date: May 1, 1997

[30] Foreign Application Priority Data

Oct. 24, 1995 [JP] Japan .................................. 7-275630

[51] Int. Cl.$^6$ .............................................. C07C 153/051
[52] U.S. Cl. ........................... 564/347; 564/74; 564/123; 564/139; 564/142; 564/166; 564/167; 564/168; 564/176; 564/349; 424/DIG. 10
[58] Field of Search .................. 558/411; 564/74, 564/123, 139, 142, 166, 167, 168, 176, 347, 349; 570/182; 424/DIG. 8

[56] References Cited

U.S. PATENT DOCUMENTS

| | | | |
|---|---|---|---|
| 2,230,691 | 2/1941 | Lewis | 252/47 |
| 3,518,305 | 6/1970 | Welch et al. | 260/558 |
| 3,828,042 | 8/1974 | Schlaudecker et al. | 260/251 |
| 3,898,272 | 8/1975 | Kurz et al. | 260/477 |
| 4,000,159 | 12/1976 | Scoggins et al. | 260/325.6 |
| 4,579,581 | 4/1986 | Kay et al. | 71/88 |
| 5,824,704 | 10/1998 | Brouwer | 514/471 |

FOREIGN PATENT DOCUMENTS

| | | |
|---|---|---|
| 0655444 | 5/1995 | European Pat. Off. . |
| 7-196633 | 8/1995 | Japan . |
| WO94/25432 | 11/1994 | WIPO . |

*Primary Examiner*—Howard C. Lee
*Attorney, Agent, or Firm*—Jordan and Hamburg LLP

[57] ABSTRACT

Disclosed are A N-[(fluoroalkoxy)phenoxyalkyl]benzamide compound represented by the formula (1):

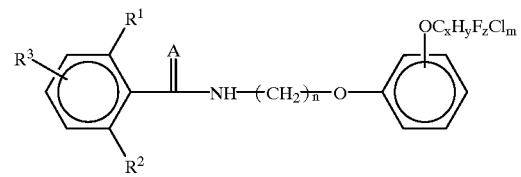

(1)

wherein $R^1$ and $R^3$ may be the same or different and represent a hydrogen atom, a halogen atom, a $C_{1-4}$ alkyl group, a $C_{1-4}$ alkoxy group, a $C_{1-4}$ haloalkyl group, a $C_{1-4}$ haloalkoxy group, a cyano group, a nitro group, or a hydroxy group; $R^2$ represents a hydrogen atom, a halogen atom, a $C_{1-4}$ alkyl group, or a $C_{1-4}$ alkoxy group; A represents an oxygen atom, or a sulfur atom; n is an integer of 1 to 6; x is 1 to 4; y is 0 to 6; z is 2 to 9; m is 0 to 2; provided that $2x+1=y+z+m$, an intermediate thereof, processes thereof and an agricultural and horticultural chemical for controlling noxious organisms containing the above-mentioned compound as an effective ingredient which is available as a nematocide, an acaricide, a fungicide, etc.

16 Claims, No Drawings

N-[(FLUOROALKOXY) PHENOXYALKYL] BENZAMIDE COMPOUNDS, INTERMEDIATES THEREOF, PROCESS FOR PRODUCING THE SAME, AND AGRICULTURAL AND HORTICULTURAL PESTICIDES

TECHNICAL FIELD

This invention relates to a novel N-[(fluoroalkoxy)-phenoxyalkyl]benzamide compound, intermediate, processes for preparing the same and an agricultural and horticultural chemical for controlling noxious organisms containing said compound as an effective ingredient useful as a nematocide, an acaricide and a fungicide.

BACKGROUND ART

As a benzamide derivative which is similar to the objective compound of the present invention, (1) and (2), etc. shown below have been known.

(1) In Japanese Provisional Patent Publication No. 105784/1989, there is a disclosure about the compound represented by the following formula:

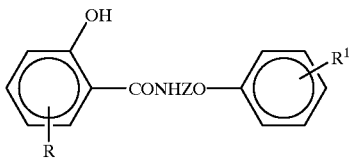

(wherein R and $R^1$ each represent a hydrogen atom, a halogen atom, a nitro group, an alkyl group, an allyl group, a cycloalkyl group, an alkoxy group or an allyloxy group; Z represents an alkylene group with the carbon number of 2 to 4. Incidentally, the R, $R^1$ and Z defined in this formula are limited only to this formula.) which is effective as a photographic material.

(2) In Japanese Provisional Patent Publication No. 151546/1989, there is a disclosure about the compound represented by the following formula:

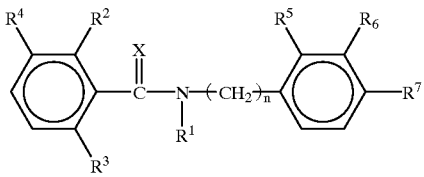

(wherein X represents O, S or NOH, $R^1$ represents H or CH, n is 1, 2 or 3, $R^2$, $R^3$ and $R^4$ are defined by either of the following paragraphs:

a) $R^2$ and $R^3$ are each Cl or Br, and $R^4$ is H:
b) $R^2$, $R^3$ and $R^4$ are each Cl or Br:
c) $R^2$ is F, $R^3$ is Cl, and $R^4$ is H: or
d) $R^2$ and $R^3$ are $CH_3$ or $C_2H_5$, and $R^4$ is H, $R^5$, $R^6$ and $R^7$ are defined by either of the following paragraphs:

a) either $R^6$ or $R^7$ is $CF_3$, and $R^5$ and the other of $R^6$ and $R^7$ are H:
b) $R^5$ and $R^6$ are H, and $R^7$ is F, Cl or Br:
c) $R^5$ and $R^7$ are each F, Cl or Br, and $R^6$ is H:
d) $R^5$ and $R^6$ are each F, Cl or Br, and $R^7$ is H:
e) $R^6$ and $R^7$ are each F, Cl or Br, and $R^5$ is H: or
f) $R^6$ is phenoxy, and $R^5$ and $R^7$ are H.

Incidentally, the $R^1$ to $R^7$, n and X defined in this formula are limited only to this formula.) which is effective as a fungicide.

As a (fluoroalkoxy)phenoxyalkylamine derivative which is similar to the starting compound of the present invention, (3) to (6), etc. shown below have been known.

(3) In Japanese Provisional Patent Publication No. 44846/1986, there is a disclosure about the compound represented by the following formula:

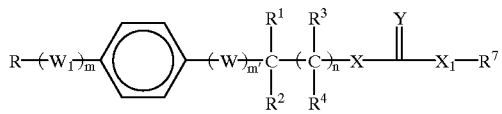

(wherein m and m' are each independently 0 or 1; n is an integer of 0 to 3; R represents $C_{1-4}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{2-10}$ alkoxyalkyl, $C_{2-10}$ alkylthioalkyl, $C_{3-8}$ cycloalkyl, $C_{3-8}$ halocycloalkyl, $C_{4-12}$ cycloalkylalkyl, heterocycloalkyl or heterocycloalkylalkyl; $R^1$ to $R^4$ and $R^8$ are each independently hydrogen or $C_{1-8}$ alkyl; $R^7$ is $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{3-8}$ cycloalkyl, $C_{4-12}$ cycloalkylalkyl or phenyl which are all unsubstituted, or a phenyl in which 1, 2 or 3-position of the carbon atom of the ring is substituted by a group selected from $C_{1-8}$ alkyl, $C_{1-8}$ haloalkyl, $C_{1-8}$ alkoxy, $C_{1-8}$ haloalkoxy, halogen, nitro, cyano and $C_{1-8}$ alkylthio, provided that when $X^1$ is $NR^9$, $R^7$ can be also selected from a substituted or unsubstituted phenylthio and a S—C($SH_3$)$_2$—CN group; $R^9$ is a hydrogen atom, or that selected from the definition of $R^7$; W represents oxygen, sulfur, $NR^8$, $CR^3R^4$ or carbonyl; $W^1$ represents oxygen, sulfur, $NR^8$, $CR^3R^4$, carbonyl, sulfinyl or sulfonyl; X and Y are each oxygen, sulfur or $NR^8$; $X^1$ represents oxygen, sulfur or $NR^9$; and Z represents $C_{1-8}$ alkyl, $C_{1-8}$ haloalkyl or halogen. Incidentally, the m, m', n, R, $R^1$ to $R^9$, W, $W^1$, X, $X^1$, Y and Z defined in this formula are limited only to this formula.) which is effective as an insecticide.

(4) In Japanese Provisional Patent Publication No. 2568470/1986, there is a disclosure about the compound represented by the following formula:

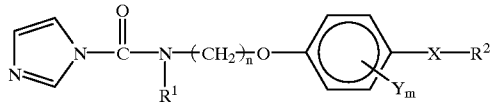

(wherein $R^1$ represents a lower alkyl group, a lower alkoxy-lower alkyl group or a cycloalkyl group having the carbon number of 3 to 8; $R^2$ represents a fluoro substituted-lower alkyl group; X represents an oxygen atom or a sulfur atom; Y represents a halogen atom or a lower alkyl group; m represents 0, 1 or 2; and n is an integer of 2 to 6.

Incidentally, the $R^1$, $R^2$, X, Y, m and n defined in this formula are limited only to this formula.) which is effective as a fungicide.

(5) In Japanese Provisional Patent Publication No. 149659/1987, there is a disclosure about the compound represented by the following formula:

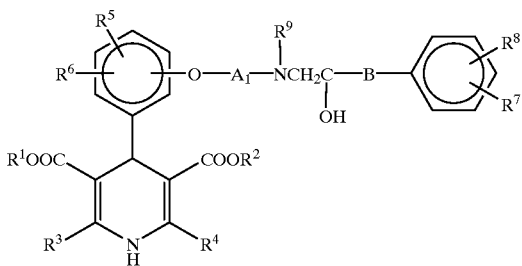

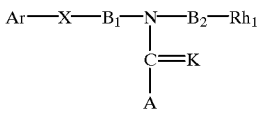

(wherein Ar represents a phenyl group which is unsubstituted or substituted by one or more of halogen, $C_{1-3}$ alkyl, $C_{1-3}$ haloalkyl, $C_{2-4}$ alkenyl, $C_{2-4}$ haloalkenyl, $C_{1-3}$ alkoxy or $C_{1-4}$ haloalkoxy as a substituent, or a pyridyl group which is unsubstituted or substituted by one or more of halogen or $C_{1-3}$ haloalkyl as a substituent; K, X and Z each independently represent O or S; $B_1$ and $B_2$ are the same or different and represent $C_{1-6}$ alkylidene; $Rh_1$ represents $C_{1-6}$ haloalkyl having 1 to 9 halogen atoms, $C_{1-6}$ haloalkenyl having 1 to 9 halogen atoms, $C_{3-8}$ haloalkoxyalkyl, $C_{3-8}$ haloalkoxyalkenyl (halogen is preferably fluorine); A represents a heterocyclic ring described in the following Table 1 (wherein $R^1$ to $R^3$ may be the same or different and represent H, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl; G represents CH or N.). Incidentally, the Ar, K, X, Z, $B_1$, $B_2$, $RH_1$, A, $R^1$ to $R^3$ and G defined in this formula are limited only to this formula.) which is effective as a fungicide.

(wherein $R^1$ and $R^2$ represent the same or different lower alkyl group; $R^3$ and $R^4$ represent the same or different lower alkyl group; $R^5$ and $R^6$ are the same or different and represent a hydrogen atom, a nitro group, a cyano group, a halogeno-lower alkyl group, a lower alkenyl group, a hydroxy group, a halogeno-lower alkoxy group, a lower alkenyloxy group, an aralkyloxy group, an aralkenyloxy group, a carboxyl group, a lower alkoxycarbonyl group, a group represented by the following formula:

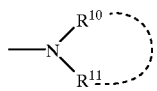

(wherein $R^{10}$ and $R^{11}$ are the same or different and represent a hydrogen atom or a lower alkyl group. Provided that $R^{10}$ and $R^{11}$ may form with the adjacent nitrogen atom a pyrrolidine ring, a piperidine ring, a morpholine ring, or a piperazine ring in which the nitrogen atom at the 4-position may be substituted by a lower alkyl group.) or a group represented by the following formula:

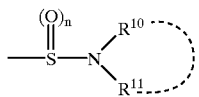

(wherein $R^{10}$ and $R^{11}$ are the same as defined above.); $R^7$ and $R^8$ are the same or different and represent a hydrogen atom, a halogen atom, a cyano group, a lower alkyl group, a hydroxy group, a lower alkoxy group, a lower alkanoylamino group, or a naphthyl group fused with a benzene ring when it is adjacent to; $A_1$ represents an alkylene group, an alkenylene group, or an alkynylene group; $R^9$ represents a hydrogen atom or a lower alkyl group; B represents a single bond or $CH_2O$; and n represents 0, 1 or 2. Provided that when $R^5$ and $R^6$ are the same or different and represent a hydrogen atom or a nitro group, $R^9$ represents a lower alkyl group or $A_1$ represents a branched alkylene group, an alkenylene group or a branched alkynylene group. Incidentally, the $R^1$ to $R^{11}$, $A_1$, B, m and n defined in this formula are limited only to this formula.) which has a calcium antagonism and a sympathetic nerve β-acceptor blocking action.

(6) In Japanese Provisional Patent Publication No. 142772/1990, there is a disclosure about the compound represented by the following formula:

TABLE 1

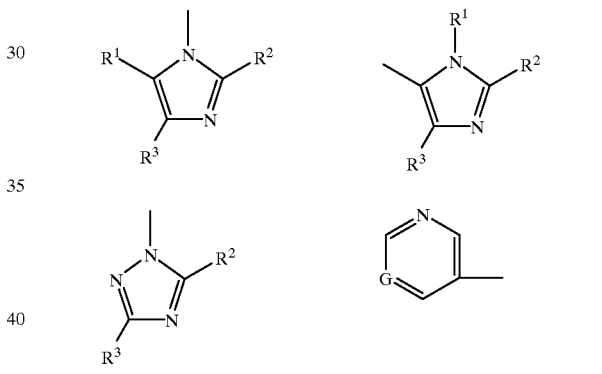

However, the disclosure of N-[(fluoroalkoxy) phenoxyalkyl]benzamide derivative and (fluoroalkoxy) phenoxyalkylamine derivative in which the amine portion is a (fluoroalkoxy)phenoxyalkylamino group as in the present invention cannot be admitted.

Accordingly, the N-[(fluoroalkoxy)phenoxyalkyl] benzamide derivative and (fluoroalkoxy) phenoxyalkylamine derivative of the present invention are novel compounds, and it has been not known that the N-[(fluoroalkoxy)-phenoxyalkyl]benzamide derivative has an effect of controlling noxious organisms for agricultural and horticultural chemical which is available as a nematocide, an acaricide, fungicide, etc.

DISCLOSURE OF THE INVENTION

An object of the present invention is to provide an agricultural and horticultural chemical for controlling noxious organisms containing the novel N-[(fluoroalkoxy)-phenoxyalkyl]benzamide derivative as an effective ingredient, which is useful as a nematocide, an acaricide, a fungicide, etc.

The present inventors have investigated to solve the above-mentioned problems, and as the results, they have found that the novel N-[(fluoroalkoxy)phenoxyalkyl]

benzamide derivative has a remarkable controlling activity as an agricultural and horticultural chemical for controlling noxious organisms which is useful as a nematocide, an acaricide, a fungicide, etc., and thus, accomplished the present invention.

That is, the present invention is as mentioned below.

The first invention relates to a N-[(fluoroalkoxy)-phenoxyalkyl]benzamide derivative represented by the following formula (1):

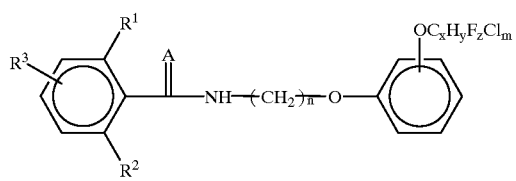

(1)

wherein $R^1$ represents a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group, a nitro group, or a hydroxy group;

$R^2$ represents a hydrogen atom, a halogen atom, an alkyl group having 1 to 4 carbon atom, or an alkoxy group having 1 to 4 carbon atom;

$R^3$ represents a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group, or a nitro group;

A represents an oxygen atom, or a sulfur atom;

n represents an integer of 1 to 6;

x represents an integer of 1 to 4;

y represents an integer of 0 to 6;

z represents an integer of 2 to 9;

m represents an integer of 0 to 2; provided that $2x+1=y+z+m$.

The second invention relates to a process for preparing the N-[(fluoroalkoxy)phenoxyalkyl]benzamide derivative in which A represents an oxygen atom in the above-mentioned formula (1) which comprises reacting a (fluoroalkoxy) phenoxyalkylamine compound represented by the following formula (2):

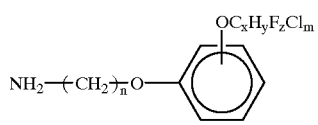

(2)

wherein n, x, y, z and m have the same meanings as defined above, and a carboxylic acid compound represented by the following formula (3):

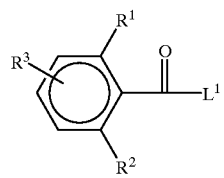

(3)

wherein $R^1$ to $R^3$ have the same meanings as defined above; and $L^1$ represents a halogen atom, or a hydroxy group.

The third invention relates to the (fluoroalkoxy) phenoxyalkylamine compound represented by the following formula (2):

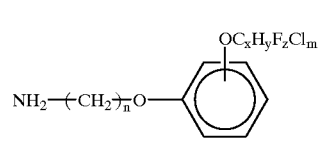

(2)

wherein n, x, y, z and m have the same meaning as defined above.

The fourth invention relates to a process for preparing the (fluoroalkoxy)phenoxyalkylamine compound represented by the above formula (2) which comprises subjecting a (fluoroalkoxy)phenoxyalkyl compound represented by the following formula (4):

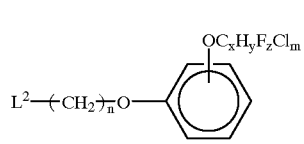

(4)

wherein $L^2$ represents a halogen atom, a methanesulfonyloxy group, or a toluenesulfonyloxy group; n, x, y, z and m have the same meanings as defined above, to amination.

The fifth invention relates to an agricultural and horticultural chemical for controlling noxious organisms containing the N-[(fluoroalkoxy)phenoxyalkyl]benzamide derivative represented by the above formula (1) as an effective ingredient.

BEST MODE FOR PRACTICING THE INVENTION

In the following, the present invention is explained in detail.

$R^1$ to $R^3$, A, x, y, z, m, n, $L^1$ and $L^2$ shown in the novel N-[(fluoroalkoxy)phenoxyalkyl]benzamide compound (Compound (1)) and starting materials for producing the same (Compound (2) to Compound (5)) and $L^3$ in the formula (6) mentioned below are as follows: ($R^1$)

As $R^1$, there may be mentioned a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group, a nitro group or a hydroxy group.

As the halogen atom, a chlorine atom, an iodine atom, a bromine atom, a fluorine atom, etc. may be mentioned but a fluorine atom, a chlorine atom and a bromine atom are preferred.

As the alkyl group, a straight or branched may be mentioned; but a methyl group is preferred.

As the alkoxy group, a straight or branched may be mentioned; but a methoxy group is preferred.

As the haloalkyl group, a straight or branched may be mentioned; and as the halogen atom, a chlorine atom, an iodine atom, a bromine atom, a fluorine atom, etc. may be mentioned, preferably a fluorine atom, and as the alkyl portion, it is preferably methyl. And as the haloalkyl group, it is preferably $CF_3$.

As the haloalkoxy group, a straight or branched may be mentioned; and as the halogen atom, a chlorine atom, an iodine atom, a bromine atom, a fluorine atom, etc. may be mentioned, preferably a fluorine atom, and as the alkyl portion, it is preferably methyl. And as the haloalkoxy group, it is preferably $CHF_2O$ or $CF_3O$. ($R^2$)

As $R^2$, there may be mentioned a hydrogen atom, a halogen atom, an alkyl group having 1 to 4 carbon atoms or an alkoxy group having 1 to 4 carbon atoms.

As the halogen atom, a chlorine atom, an iodine atom, a bromine atom, a fluorine atom, etc. may be mentioned but a fluorine atom is preferred.

As the alkyl group, a straight or branched may be mentioned; but a methyl group is preferred.

As the alkoxy group, a straight or branched may be mentioned; but a methoxy group is preferred. ($R^3$)

As $R^3$, there may be mentioned a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group or a nitro group.

As the halogen atom, a chlorine atom, an iodine atom, a bromine atom, a fluorine atom, etc. may be mentioned.

As the alkyl group, a straight or branched may be mentioned.

As the alkoxy group, a straight or branched may be mentioned.

As the haloalkyl group, a straight or branched may be mentioned; and as the halogen atom, a chlorine atom, an iodine atom, a bromine atom, a fluorine atom, etc. may be mentioned, preferably a fluorine atom, and as the alkyl portion, it is preferably methyl. And as the haloalkyl group, it is preferably $CF_3$.

As the haloalkoxy group, a straight or branched may be mentioned; and as the halogen atom, a chlorine atom, an iodine atom, a bromine atom, a fluorine atom, etc. may be mentioned, preferably a fluorine atom, and as the alkyl portion, it is preferably methyl. And as the haloalkoxy group, it is preferably $CF_3O$.

The substitution position of $R^3$ is not particularly limited but preferably 4-position. ($OC_xH_yF_zCl_m$)

x is an integer of 1 to 4, preferably 1 to 3.

y is an integer of 0 to 6, preferably 0 to 4.

z is an integer of 2 to 9, preferably 2 to 6.

m is an integer of 0 to 2.

Provided that $2x+1=y+z+m$.

The substitution position of $OC_xH_yF_zCl_m$ is not particularly limited but preferably 3-position or 4-position. (A)

As A, an oxygen atom or a sulfur atom may be mentioned. (n)

n is an integer of 1 to 6, preferably 2 to 5, further preferably 2 or 3. ($L^1$ to $L^3$)

As $L^1$, a halogen atom or a hydroxyl group may be mentioned, and the halogen atom may include a chlorine atom and a bromine atom.

As $L^2$ and $L^3$, a halogen atom, a methanesulfonyloxy group or a toluenesulfonyloxy group may be mentioned, and the halogen atom may include a chlorine atom and a bromine atom.

As the compound (1), those in which the above-mentioned various kinds of substituents are employed in combination may be mentioned, but preferred in view of pharmaceutical effects are as follows.

(a) Compound (1) in which $R^1$ to $R^3$ are hydrogen atoms, $OC_xH_yF_zCl_m$ is 3-$OC_xF_z$ or 4-$OC_xF_z$, A is an oxygen atom and n is 2.

(b) Compound (1) in which $R^1$ is a hydrogen atom, $R^2$ and $R^3$ are hydrogen atoms, $OC_xH_yF_zCl_m$ is 3-$OC_xF_z$ or 4-$OC_xF_z$, A is an oxygen atom and n is 2.

(c) Compound (1) in which $R^1$ and $R^2$ are hydrogen atoms, $R^3$ is a halogen atom, $OC_xH_yF_zCl_m$ is 3-$OC_xF_z$ or 4-$OC_xF_z$, A is an oxygen atom and n is 2.

(d) Compound (1) in which $R^1$ and $R^2$ are halogen atoms, $R^3$ is a hydrogen atom, $OC_xH_yF_zCl_m$ is 3-$OC_xF_z$ or 4-$OC_xF_z$, A is an oxygen atom and n is 2.

(e) Compound (1) in which $R^1$ and $R^3$ are halogen atoms, $R^2$ is a hydrogen atom, $OC_xH_yF_zCl_m$ is 3-$OC_xF_z$ or 4-$OC_xF_z$, A is an oxygen atom and n is 2.

(f) Compound (1) in which $R^1$ to $R^3$ are halogen atoms, $OC_xH_yF_zCl_m$ is 3-$OC_xF_z$ or 4-$OC_xF_z$, A is an oxygen atom and n is 2.

(g) Compound (1) in which $R^1$ is an alkyl group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2.

(h) Compound (1) in which $R^1$ is an alkoxy group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2.

(i) Compound (1) in which $R^1$ is a haloalkyl group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2.

(j) Compound (1) in which $R^1$ and $R^2$ are halogen atoms, $R^3$ is a hydrogen atom, $OC_xH_yF_zCl_m$ is 4-$OC_xH_yF_z$, A is an oxygen atom and n is 2.

(k) Compound (1) in which $R^1$ and $R^2$ are halogen atoms, $R^3$ is a hydrogen atom, $OC_xH_yF_zCl_m$ is 4-$OC_xH_yF_zCl_m$, A is an oxygen atom and n is 2.

(l) Compound (1) in which $R^1$ and $R^2$ are halogen atoms, $R^3$ is a hydrogen atom, $OC_xH_yF_zCl_m$ is 3-$OC_xF_z$ or 4-$OC_xF_z$, A is a sulfur atom and n is 2.

(m) Compound (1) in which $R^1$ is a haloalkoxy group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2.

(n) Compound (1) in which $R^1$ is a nitro group, $R^2$ and $R^3$ are hydrogen atoms, $OC_xH_yF_zCl_m$ is 3-$OC_xF_z$ or 4-$OC_xF_z$, A is an oxygen atom and n is 2.

(o) Compound (1) in which $R^1$ and $R^2$ are an alkyl group having 1 to 4 carbon atoms, $R^3$ is a hydrogen atom, $OC_xH_yF_zCl_m$ is 3-$OC_xF_z$ or 4-$OC_xF_z$, A is an oxygen atom and n is 2.

(p) Compound (1) in which $R^1$ and $R^2$ are an alkoxy group having 1 to 4 carbon atoms, $R^3$ is a hydrogen atom, $OC_xH_yF_zCl_m$ is 3-$OC_xF_z$ or 4-$OC_xF_z$, A is an oxygen atom and n is 2.

(q) Compound (1) in which $R^1$ is a hydroxyl group, $R^2$ and $R^3$ are hydrogen atoms, $OC_xH_yF_zCl_m$ is 3-$OC_xF_z$ or 4-$OC_xF_z$, A is an oxygen atom and n is 2.

(r) Compound (1) in which $R^1$ is a hydroxyl group, $R^2$ is a hydrogen atom, $R^3$ is a halogen atom, $OC_xH_yF_zCl_m$ is 3-$OC_xF_z$ or 4-$OC_xF_z$, A is an oxygen atom and n is 2.

(s) Compound (1) in which $R^1$ and $R^3$ are halogen atoms, $R^2$ is a hydrogen atom, $OC_xH_yF_zCl_m$ is 3-$OC_xH_yF_zCl_m$ or 4-$OC_xF_z$, A is an oxygen atom and n is 3.

As Compound (1) represented by these (a) to (s), preferred ones shown at the explanation for the above-mentioned $R^1$ to $R^3$, A, x, y, z, m, and n, and more preferred ones may be exemplified.

Specific compounds (1) of these may include Compounds {(1-1) to (1-4), (1-8), (1-10), (1-13) to (1-17), (1-19), (1-30), (1-35), (1-38), (1-40), (1-43), (1-46), (1-52), (1-53), (1-55), (1-56)} described in the following Table 3, etc.

As preferred embodiments for producing the N-[(fluoroalkoxy)phenoxyalkyl]benzamide compound represented by the above formula (1), in addition to the synthetic method 1 described as the second invention, the following two kinds of methods (Synthetic methods 2 and 3) may be mentioned. (Synthetic method 2)

A process for producing a N-[(fluoroalkoxy)phenoxyalkyl]benzamide compound represented by the above formula (1) which comprises reacting a benzamide compound represented by the following formula (5):

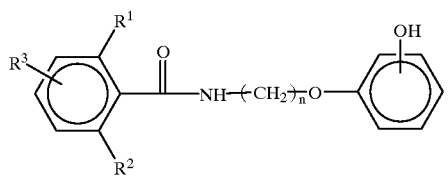

(5)

wherein $R^1$ to $R^3$, A and n are the same as mentioned above, with a fluoroalkyl compound represented by the following formula (6):

(6)

wherein represents a halogen atom, a methanesulfonyl group and a toluenesulfonyloxy group; x, y and z have the same meanings as defined above, in the presence of a base.
(Synthetic Method 3)

A process for producing a N-[(fluoroalkoxy)phenoxyalkyl]benzamide compound (referred to as Compound (1-b)) in which A represents a sulfur atom in the above-mentioned formula (1) which comprises reacting a compound (1a) represented by the following formula (1a):

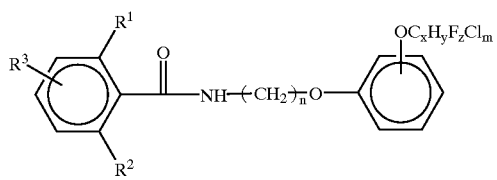

(1a)

wherein $R^1$ to $R^3$, x, y, z, m and n have the same meanings as mentioned above, in the presence of a sulfurizing agent.

The above-mentioned synthetic methods 1 to 3 of Compound (1) of the present invention will be explained in more detail.
(Synthetic Method 1)

The synthetic method is as shown in Synthetic method 1, Compound (2) and Compound (3) are reacted in the presence of a base or a condensing agent in a solvent or without any solvent or a condensing agent to obtain the desired compound (1a) (A compound in which A in Compound (1) is represented by the formula (1).

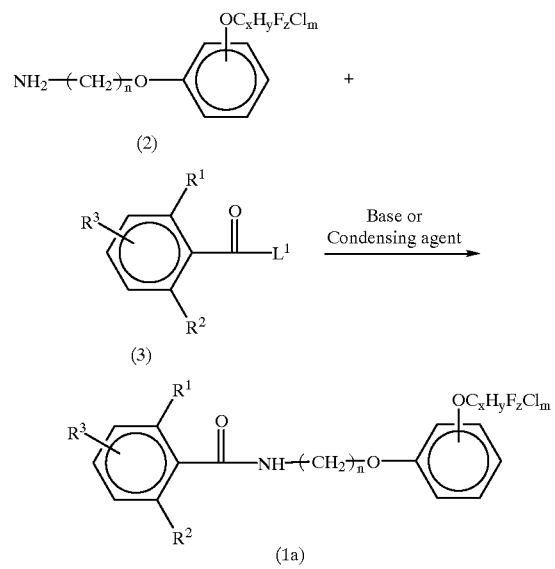

wherein $R^1$ to $R^3$, x, y, z, m and n have the same meanings as mentioned above,
(1) In case where $L^1$ is a halogen atom The above process can be performed by reacting Compound (2) and Compound (3) in a solvent or without solvent, in the presence of a base.

As the kinds of the solvent, it is not particularly limited so long as it does not directly participate the present reaction, and it may include, for example, an aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene, cyclohexane, etc.; ethers such as diethyl ether, tetrahydrofuran, dioxane, etc.; ketones such as acetone, methyl ethyl ketone, etc.; nitrites such as acetonitrile, propionitrile, etc.; organic bases such as triethylamine, pyridine, N,N-dimethylaniline, etc.; polar solvents such as N,N-dimethylformamide, N,N-dimethylacetamide, dimethyl-sulfoxide, dimethylimidazolidinone, etc.; water; mixture of the above mentioned solvents, etc.

Among these solvents, preferred are hydrocarbons and ethers.

An amount of the solvent may preferably set so as to become Compound (2) being 5 to 80% by weight; preferably 10 to 70% by weight.

A molar ratio of the starting materials can be set optionally, but usually Compound (3) is used in a ratio of 0.5 to 2 moles per 1 mole of Compound (2).

The kind of the base is not specifically limited, and, for example, organic bases such as triethylamine, pyridine, N,N-dimethylaniline, 1,8-diazabicyclo[5.4.0]-7-undecene (DBU), etc.; and inorganic bases such as sodium hydride, sodium amide, sodium hydroxide, potassium hydroxide, sodium carbonate, sodium hydrogen carbonate, potassium carbonate, etc. may be mentioned An amount of the base to be used is 1 to 10-fold mole based on Compound (2) and preferably 1 to 5-fold mole.

The reaction temperature is not particularly limited, but a temperature range of from an ice-cooling temperature to the boiling point of the solvent to be used or less, preferably 0 to 30° C.

The reaction time may vary depending on the above-mentioned concentration and the temperature, but it is usually 0.1 to 2 hours.

The starting Compound (2) can be obtained as shown below by reacting Compound (4) and potassium phthalimide in a solvent (First step), and then reacting a hydrazine (Second step).

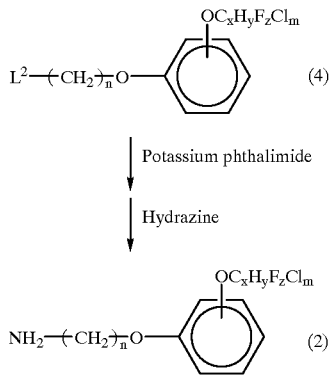

wherein $L^2$, n, x, y, z and m have the same meaning as defined above.

First Step

The kind of the solvent to be used in the first step is not particularly limited so long as it does not participate the present reaction directly, and, for example, hydrocarbons, ethers, ketones, nitrites, polar solvents and admixture of the above solvents as described in the above-mentioned (1) may be mentioned.

An amount of potassium phthalimide is 1 to 10-fold mole based on Compound (4), preferably 1 to 5-fold mole.

The reaction temperature is not particularly limited, but it is a temperature range of from an ice-cooling temperature to the boiling point of the solvent to be used or less, preferably 40 to 120° C.

The reaction time may vary depending on the above-mentioned concentration and the temperature, but it is usually 0.5 to 10 hours.

Second Step

The reaction with hydrazine can be carried out by isolating the phthalimide derivative obtained by the above-mentioned first step or without isolation.

The kind of the solvent to be used in the second step is not particularly limited so long as it does not participate the present reaction directly, and, for example, hydrocarbons; ethers; polar solvents; alcohols such as methanol, ethanol, propanol, butanol, etc.; water; and admixture of the above-mentioned solvents as described in the above-mentioned (1) may be mentioned.

An amount of hydrazine is 1 to 10-fold mole based on Compound (4), preferably 1 to 5-fold mole.

The reaction temperature is not particularly limited, but it is a temperature range of from an ice-cooling temperature to the boiling point of the solvent to be used or less, preferably 40 to 120° C.

The reaction time may vary depending on the above-mentioned concentration and the temperature, but it is usually 0.5 to 10 hours.

Compound (2) prepared as mentioned above is subjected to the usual post-treatment such as extraction, concentration, filtration, etc. after completion of the reaction, and optionally purified by the well-known means such as recrsytallization, various kinds of chromatographies, etc., if necessary.

Compound (4) can be obtained by subjecting the reaction as mentioned below.

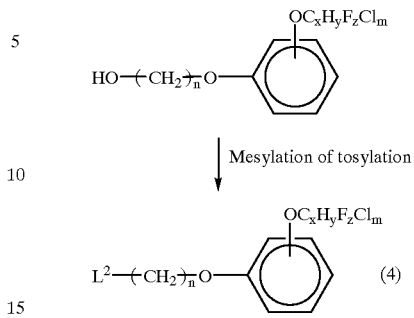

wherein n, x, y, z, m and $L^2$ have the same meanings as defined above.

Also, Compound (4) can be also obtained by carrying out the reaction as mentioned below.

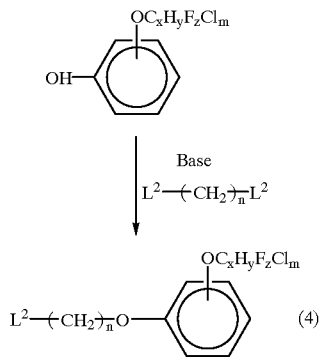

wherein n, x, y, z, m and $L^2$ have the same meanings as defined above.

As Compound (3), a commercially available product can be used.

(2) When $L^1$ is a hydroxyl group

The above-mentioned process can be performed by reacting Compound (2) and Compound (3) in a solvent or without solvent in the presence of a condensing agent.

The kind of the solvent is not particularly limited so long as it does not participate the present reaction directly, and, for example, hydrocarbons, ethers, ketones, nitrites, polar solvents and admixture of the above solvents which are the same as described in the above-mentioned (1) may be used.

An amount of the solvent may be so used that Compound (2) becomes 5 to 80% by weight; preferably 10 to 70% by weight.

A ratio of the starting materials can be set optionally, but usually Compound (3) is in a ratio of 0.5 to 2 moles based on 1 mole of Compound (2).

The kind of the dehydrating agent is not particularly limited, and for example, there may be mentioned dicyclohexylcarbodiimide (DCC), diethylazodicarboxylate, diisopropylazodicarboxylate, 1-ethyl-3-(3-dimethylaminopropyl)-carbodiimide hydrochloride (WSC), 1,1'-carbonyldiimidazole, sulfuric acid, phosphorus pentachloride, etc.

An amount of the dehydrating agent is 1 to 10-fold mole based on Compound (2), and preferably 1 to 5-fold mole.

The reaction temperature is not particularly limited, but it is a temperature range of from an ice-cooling temperature to the boiling point of the solvent to be used or less, preferably 0 to 50° C.

The reaction time may vary depending on the above-mentioned concentration and the temperature, but it is usually 0.5 to 8 hours.

Compound (1a) prepared as mentioned above is subjected to the usual post-treatment such as extraction, concentration, filtration, etc. after completion of the reaction, and optionally purified by the well-known means such as recrsytallization, various kinds of chromatographies, etc., if necessary.

(Synthethic Method 2)

Synthetic method 2 is as shown below a method of obtaining Compound (1a) (a compound in Compound (1) where A is represented by an oxygen atom) by reacting Compound (5) and Compound (6) in a solvent in the presence of a base.

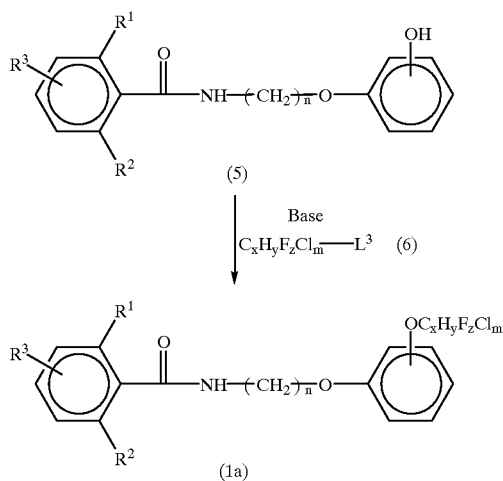

wherein $R^1$ to $R^3$, n, x, y, z, m and $L^3$ have the same meanings as defined above.

The kind of the solvent is not particularly limited so long as it does not participate the present reaction directly, and, for example, hydrocarbons, ethers, ketones, nitriles, polar solvents and admixture of the above solvents which are the same as described in the above-mentioned Synthetic method 1 may be mentioned.

An amount of the solvent may be so used that Compound (5) becomes 5 to 80% by weight; preferably 10 to 70% by weight.

The kind of the base is not particularly limited and there may be mentioned, for example, the organic base and the inorganic base mentioned in the above (1), and preferably sodium hydroxide and potassium hydroxide.

An amount of the base is 1 to 10-fold moles based on Compound (5) and preferably 2 to 5-fold moles.

The reaction temperature is not particularly limited, but it is a temperature range of from an ice-cooling temperature to the boiling point of the solvent to be used or less, preferably 0 to 100° C.

The reaction time may vary depending on the above-mentioned concentration and the temperature, but it is usually 0.5 to 3 hours.

Also, when the materials are reacted in a two-layer system of an organic solvent and water, the reaction can be promoted by using a phase-transfer catalyst.

The phase-transfer catalyst is not particularly limited, and there may be mentioned, for example, tetrabutylammonium bromide, benzyltriethylammonium chloride, tricaprylylmethylammonium chloride, etc.

An amount of the phase-transfer catalyst is 0.01 to 5-fold moles based on Compound (5), preferably 0.05 to 0.5-fold mole.

Compound (1a) prepared as mentioned above is subjected to the usual post-treatment such as extraction, concentration, filtration, etc. after completion of the reaction, and optionally purified by the well-known means such as recrsytallization, various kinds of chromatographies, etc., if necessary.

Compound (5) can be obtained by effecting the reaction as mentioned below.

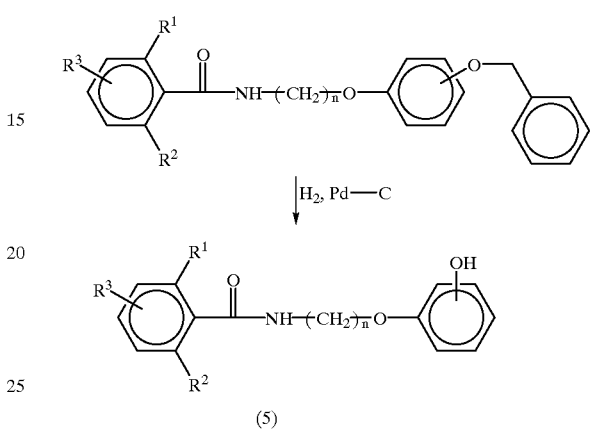

wherein $R^1$ to $R^3$ and n have the same meanings as defined above.

As Compound (6), a commercially available product may be used, but it can be also obtained by effecting the reaction as mentioned below.

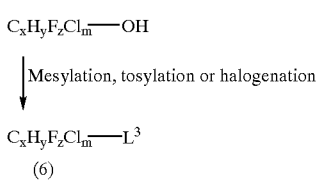

wherein x, y, z, m and $L^3$ have the same meanings as defined above.

(Synthetic Method 3)

Synthetic method 3 is a method, as mentioned below, in which Compound (1b) (a compound in which A in Compound (1) is shown by a sulfur atom) is obtained by reacting Compound (1a) in a solvent in the presence of a sulfurizing agent.

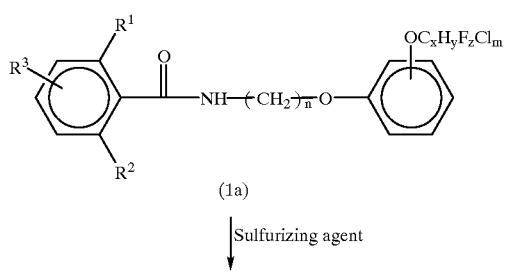

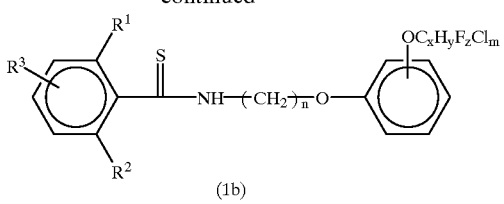

(1b)

wherein $R^1$ to $R^3$, n, x, y, z and m have the same meanings as defined above.

The kind of the solvent is not particularly limited so long as it does not participate the present reaction directly, and, for example, hydrocarbons, ethers and admixture of the above solvents which are the same as described in the above-mentioned Synthetic method 1 may be mentioned.

An amount of the solvent may be so used that Compound (1a) becomes 5 to 80% by weight; preferably 10 to 70% by weight.

The kind of the sulfurizing agent is not particularly limited and there may be mentioned, for example, phosphorus pentasulfate, 2,4-bis(4-methoxyphenyl)-1,3-dithia-2,4-diphosphetan-2,4-disulfide (Lawesson's reagent), hydrogen sulfide, etc.

An amount of the sulfurizing agent is 1 to 10-fold moles based on Compound (1a) and preferably 1 to 5-fold moles.

The reaction temperature is not particularly limited, but it is a temperature range of from an ice-cooling temperature to the boiling point of the solvent to be used or less, preferably 40 to 120° C.

The reaction time may vary depending on the above-mentioned concentration and the temperature, but it is usually 0.5 to 10 hours.

Compound (1b) prepared as mentioned above is subjected to the usual post-treatment such as extraction, concentration, filtration, etc. after completion of the reaction, and optionally purified by the well-known means such as recrystallization, various kinds of chromatographies, etc., if necessary.

As the agricultural and horticultural noxious organisms on which a controlling effect by the compound (I) of the present invention can be observed, there may be mentioned agricultural and horticultural noxious insects (e.g. Hemiptera (planthoppers, leafhoppers, aphides, white-flies, etc.), Lepidoptera (cabbage armyworms, diamond-back moth, leafroller moths, pyralid moths, common cabbage worm, etc.), Coleoptera (Tenebrionid beetles, leafbeetles, weevils, scarabs,.etc.) and Acarina (citrus red mite, two-spotted spider mite, etc. of Tetranychidae family, pink citrus rust mite of Eriophyidae family, etc.)), hygienically noxious insects (e.g. flies, mosquitoes, cockroaches, etc.), noxious insects of stored grains (rust-red flour beetles, bean weevils, etc.), and root knot nematode, pine wood nematode and bulb mite in soil, and also agricultural and horticultural diseases (e.g. wheat brown rust, barley powdery mildew, cucumber downy mildew, rice blast, tomato late blight, etc.).

The agricultural and horticultural chemical for controlling noxious organisms of the present invention is particularly remarkable in nematocidal, acaricidal and fungicidal effect and contains at least one kind of Compound (1) as an effective ingredient.

Compound (1) may be used singly, but usually, it is preferred to formulate a carrier, surfactant, dispersant, auxiliary, etc. (for example, it is prepared as a composition such as dust powder, an emulsifiable concentrate, a fine granule, a granule, a wettable powder, an oily suspension, an aerosol, etc.) according to the conventionally known method.

As the carrier, there may be mentioned, for example, a solid carrier such as bentonite, clay, kaolin, diatomaceous earth, white carbon, vermiculite, calcium hydroxide, siliceous sand, ammonium sulfate,.urea, etc., a liquid carrier such as hydrocarbon (kerosine, mineral oil, etc.), aromatic hydrocarbon, (benzene, toluene, xylene, etc.), chlorinated hydrocarbon (chloroform, carbon tetrachloride, etc.), ethers (dioxane, tetrahydrofuran, etc.), ketones (acetone, cyclohexanone, isophorone, etc.), esters (ethyl acetate, ethyleneglycol acetate, dibutyl maleate, etc.), alcohols (methanol, n-hexanone, ethylene glycol, etc.), polar solvent (dimethylformamide, dimethylsulfoxide, etc.), water, etc.; a gas carrier such as air, nitrogen, a carbonic acid gas, fleone, etc. (in this case, mixture spreading can be carried out), and the like.

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

In the following, the present invention is explained by referring to Examples more specifically. These Examples are not intended to limit the scope of the present invention.

Example 1

(Synthesis of Compound (2))

(1) Synthesis of 2-(4-trifluoromethoxyphenoxy)ethylamine (Compound (2-2))

In N,N-dimethylformamide (20 ml) was dissolved methanesulfonic acid 2-(4-trifluoromethoxyphenoxy)ethyl ester (3.00 g), then potassium phthalimide (2.04 g) was added thereto and the mixture was stirred at 100° C. for 3 hours.

After completion of the reaction, water (100 ml) was added to the mixture and the resulting mixture was stirred, and formed precipitates were taken out by filtration.

The resulting precipitates were dissolved by adding ethanol (30 ml) under heating, then hydrazine hydrate (0.55 g) was added thereto and the mixture was refluxed for 3 hours under heating.

After completion of the reaction, ethanol was removed under reduced pressure, then a 5N sodium hydroxide aqueous solution (50 ml) was added to the precipitates to dissolve the precipitates and the mixture was extracted with ethyl acetate.

Then, the organic layer was washed with a saturated saline solution, dried over anhydrous sodium sulfate and the solvent was removed under reduced pressure, and the residue was purified by silica gel chromatography (Wako gel C-200, eluted by ethyl acetate and subsequently by ethanol) to obtain 1.54 g of the title compound as a pale yellowish oily product.

$^1$H-NMR (CDCl$_3$, δ ppm)

2.18 to 2.47 (2H, br), 3.11 (2H, t, J=5.1 Hz), 3.91 to 4.09 (2H, m), 6.88 to 7.25 (4H, m)

(2) Synthesis of 2-[4-(2,2,2-trifluoroethoxy)phenoxy]ethylamine (Compound (2-3))

In N,N-dimethylformamide (30 ml) was dissolved 2-[4-(2,2,2-trifluoroethoxy)phenoxy]ethyl bromide (4.50 g), then potassium phthalimide (3.05 g) was added thereto and the mixture was stirred at 100° C. for 3 hours.

After completion of the reaction, water (120 ml) was added to the mixture and the resulting mixture was stirred, and formed precipitates were taken out by filtration.

The resulting precipitates were dissolved by adding ethanol (50 ml) under heating, then hydrazine hydrate (0.55 g) was added thereto and the mixture was refluxed for 3 hours under heating.

After completion of the reaction, 5N hydrochloric acid (50 ml) was added to the mixture, and the resulting mixture was stirred and then filtered under heating.

The resulting filtrate was washed with toluene, then the aqueous layer was made basic with a 5N sodium hydroxide aqueous solution, and the title compound was extracted with ethyl acetate.

Then, the organic layer was washed with a saturated saline solution, dried over anhydrous sodium sulfate and the solvent was removed under reduced pressure to obtain 2.57 g of the title compound as a pale yellowish oily product.

$^1$H-NMR (CDCl$_3$, δ ppm)

1.39 to 1.54 (2H, br), 2.95 to 3.13 (2H, m), 3.87 to 4.37 (4H, m), 6.74 to 6.97 (4H, m)

(3) Synthesis of 2-[4-(1,1,2,2-tetrafluoroethoxy)phenoxy]ethylamine (Compound (2-5))

In N,N-dimethylformamide (10 ml) was dissolved methanesulfonic acid 2-[4-(1,1,2,2-tetrafluoroethoxy)-phenoxy]ethyl ester (1.61 g), then potassium phthalimide (1.02 g) was added thereto and the mixture was stirred at about 100° C. for 3 hours.

After completion of the reaction, water (50 ml) was added to the mixture and formed precipitates were collected by filtration, and after pulverization the precipitates, they were washed with water.

The resulting precipitates were dissolved by adding them to ethanol (20 ml) under heating, then hydrazine hydrate (0.28 g) was added thereto and the mixture was stirred for 3 hours under heating.

After completion of the reaction, ethanol was removed under reduced pressure, then a 5N sodium hydroxide aqueous solution (30 ml) was added to the precipitates to dissolve the precipitates and the title compound was extracted with ethyl acetate.

Then, the organic layer was washed with a saturated saline solution, dried over anhydrous sodium sulfate and ethyl acetate was removed under reduced pressure. The resulting oily product was purified by silica gel chromatography (Wako gel C-200, eluted by ethyl acetate to ethanol) to obtain 0.89 g of the title compound which is a pale yellowish oily product.

$^1$H-NMR (CDCl$_3$, δ ppm)

1.82 to 2.19 (2H, br), 3.01 to 3.20 (2H, br), 3.98 (2H, t), 5.89 (1H, m), 6.86 to 7.18 (4H, m)

(4) Synthesis of 2-[4-(2-chloro-1,1,2-trifluoroethoxy)-phenoxy]ethylamine (Compound (2- 6))

In N,N-dimethylformamide (30 ml) was dissolved 2-[4-(2-chloro-1,1,2-trifluoroethoxy)phenoxy]ethyl bromide (5.00 g), then potassium phthalimide (3.05 g) was added thereto and the mixture was stirred at 100° C. for 3 hours.

After completion of the reaction, water (120 ml) was added to the mixture and formed precipitates were taken out by filtration.

The resulting precipitates were dissolved by adding them to ethanol (50 ml) under heating, then hydrazine hydrate (0.83 g) was added thereto and the mixture was stirred for 3 hours under heating.

After completion of the reaction, 5N hydrochloric acid (70 ml) was added to the mixture, and the resulting mixture was stirred and then filtered under heating.

The resulting filtrate was washed with toluene, subsequently the aqueous layer was made basic with a 5N sodium hydroxide aqueous solution and the title compound was extracted with ethyl acetate.

Then, the organic layer was washed with a saturated saline solution, dried over anhydrous sodium sulfate and the solvent was removed under reduced pressure to obtain 2.73 g of the title compound which is a pale yellowish oily product.

$^1$H-NMR (CDCl$_3$, δ ppm)

1.18 to 1.75 (2H, br), 2.95 to 3.14 (2H, m), 3.49 (2H, t, J=4.9 Hz), 6.14 to 6.35 (1H, m), 6.74 to 7.26 (4H, m) (5) Synthesis of 2-(3-trifluoromethoxyphenoxy)ethylamine (Compound (2-9))

In N,N-dimethylformamide (20 ml) was dissolved methanesulfonic acid 2-(3-trifluoromethoxyphenoxy)ethyl ester (3.00 g), then potassium phthalimide (2.04 g) was added thereto and the mixture was stirred at 100° C. for 3 hours.

After completion of the reaction, water (100 ml) was added to the mixture and formed precipitates were taken out by filtration.

The resulting precipitates were dissolved by adding them to ethanol (30 ml) under heating, then hydrazine hydrate (0.55 g) was added thereto and the mixture was refluxed for 3 hours under heating.

After completion of the reaction, 5N hydrochloric acid (50 ml) was added to the mixture, and the resulting mixture was stirred and then filtered under heating.

The resulting filtrate was washed with toluene, subsequently the aqueous layer was made basic with a 5N sodium hydroxide aqueous solution and the title compound was extracted with ethyl acetate.

Then, the organic layer was washed with a saturated saline solution, dried over anhydrous sodium sulfate and the solvent was removed under reduced pressure to obtain 1.76 g of the title compound which is a pale yellowish oily product.

$^1$H-NMR (CDCl$_3$, δ ppm)

1.61 to 1.92 (2H, br), 3.09 (2H, t, J=5.1 Hz), 3.99 (2H, t, J=5.1 Hz), 6.67 to 7.35 (4H, m)

(6) Synthesis of 3-(4-trifluoromethoxyphenoxy)propylamine (Compound (2-10)).

In N,N-dimethylformamide (20 ml) was dissolved methanesulfonic acid 3-(4-trifluoromethoxyphenoxy)propyl ester (3.14 g), then potassium phthalimide (2.04 g) was added thereto and the mixture was stirred at 100° C. for 3 hours.

After completion of the reaction, water (100 ml) was added to the mixture and formed precipitates were taken out by filtration.

The resulting precipitates were dissolved by adding them to ethanol (30 ml) under heating, then hydrazine hydrate (0.55 g) was added thereto and the mixture was refluxed for 3 hours under heating.

After completion of the reaction, 5N hydrochloric acid (50 ml) was added to the mixture, and the resulting mixture was stirred and then filtered under heating.

The resulting filtrate was washed with toluene, subsequently the aqueous layer was made basic with a 5N sodium hydroxide aqueous solution and the title compound was extracted with ethyl acetate.

Then, the organic layer was washed with a saturated saline solution, dried over anhydrous sodium sulfate and the solvent was removed under reduced pressure to obtain 1.68 g of the title compound which is a pale yellowish oily product.

$^1$H-NMR (CDCl$_3$, δ ppm)

1.81 to 2.06 (2H, m), 2.22 to 2.51 (2H, Br), 2.93 (2H, t, J=6.6 Hz), 4.04 (2H, t, J=5.9 Hz), 6.77 to 7.24 (4H, m)

(7) Synthesis of other Compound (2) in Table 2

In accordance with either one of the above-mentioned (1) to (6). other Compound (2) in Table 2 was synthesized.

Compounds synthesized as mentioned above and physical properties thereof are shown in Table 2.

TABLE 2

$$NH-(CH_2)_n-O-\underset{}{\underset{}{\bigcirc}}-OC_xH_yF_zCl_m \quad (2)$$

| Compound | OC$_x$H$_y$F$_z$Cl$_m$ | n | Physical properties |
|---|---|---|---|
| 2-1 | 4-OCHF$_2$ | 2 | |
| 2-2 | 4-OCF$_3$ | 2 | n$_D^{20.0}$ 1.4654 |
| 2-3 | 4-OCH$_2$CF$_3$ | 2 | n$_D^{20.0}$ 1.4768 |
| 2-4 | 4-OCF$_2$CFH$_2$ | 2 | |
| 2-5 | 4-OCF$_2$CF$_2$H | 2 | n$_D^{20.0}$ 1.4688 |
| 2-6 | 4-OCF$_2$CFClH | 2 | n$_D^{20.0}$ 1.4834 |
| 2-7 | 4-OCF$_2$CHFCF$_3$ | 2 | |
| 2-8 | 2-OCF$_3$ | 2 | |
| 2-9 | 3-OCF$_3$ | 2 | n$_D^{20.0}$ 1.4635 |
| 2-10 | 4-OCF$_3$ | 3 | n$_D^{20.0}$ 1.4676 |
| 2-11 | 4-OCF$_3$ | 5 | |

Example 2

(Synthesis of Compound (1))

By using Compound (2) obtained in Example 1, the title compound (1) was synthesized.

(1) Synthesis of N-[2-(4-trifluoromethoxyphenoxy)ethyl]-2-fluorobenzamide (Compound (1-2))

WSC (1-ethyl-3-(3-dimethylaminopropyl)carbodiimide hydrochloride) (1.10 g) was added to a dichloromethane (20 ml) solution of 2-(4-trifluoromethoxyphenoxy)ethylamine (1.10 g) and 2-fluorobenzoic acid (0.70 g) and the mixture was stirred at room temperature for 3 hours.

After completion of the reaction, water (10 ml) was added to the reaction mixture and extraction was carried out. The organic layer was washed with a saturated saline solution and dried over anhydrous sodium sulfate, and then the solvent was removed under reduced pressure.

The resulting residue was purified by silica gel chromatography (Wako gel C-200, eluted by toluene : ethyl acetate= 9:1) to obtain 1.21 g of the title compound as colorless crystal.

$^1$H-NMR (CDCl$_3$, δ ppm)

3.87 to 4.22 (4H, m), 6.85 to 7.52 (8H, m), 8.06 to 8.14 (1H, m)

(2) Synthesis of N-[2-(4-trifluoromethoxyphenoxy)ethyl]-2-chlorobenzamide (Compound (1-3))

A tetrahydrofuran (5 ml) solution of 2-chlorobenzoyl chloride (0.88 g) was added dropwise under ice-cooling and stirring to a tetrahydrofuran (20 ml) solution of 2-(4-trifluoromethoxyphenoxy)ethylamine (1.10 g) and triethylamine (0.51 g) and the mixture was further stirred at room temperature for one hour.

After completion of the reaction, the formed triethylamine hydrochloride was removed by filtration, and the solvent was removed under reduced pressure.

The resulting residue was purified by silica gel chromatography (Wako gel C-200, eluted by toluene:ethyl acetate= 9:1) to obtain 1.53 g of the title compound as colorless crystal.

$^1$H-NMR (CDCl$_3$, δ ppm)

3.78 to 4.22 (4H, m), 6.52 to 6.80 (1H, br), 6.80 to 7.87 (8H, m)

(3) Synthesis of N-[2-(4-trifluoromethoxyphenoxy)ethyl]-2,6-difluorobenzamide Compound (1-10))

A tetrahydrofuran (5 ml) of 2,6-difluorobenzoyl chloride (0.88 g) was added dropwise under ice-cooling and stirring to a tetrahydrofuran (20 ml) solution of 2-(4-trifluoromethoxyphenoxy)ethylamine (1.10 g) and triethylamine (0.51 g) and the mixture was further stirred at room temperature for one hour.

After completion of the reaction, the formed triethylamine hydrochloride was removed by filtration and the solvent was removed under reduced pressure.

The resulting residue was purified by silica gel chromatography (Wako gel C-200, eluted by toluene:ethyl acetate =9:1) to obtain 1.48 g of the title compound as colorless crystal.

$^1$H-NMR (CDCl$_3$, δ ppm)

3.78 to 4.22 (4H, m), 6.28 to 6.53 (1H, br), 6.78 to 7.47 (7H, m)

(4) Synthesis of N-[2-(4-trifluoromethoxyphenoxy)ethyl]-2,4,6-trifluorobenzamide (Compound (1-14))

WSC (1.15 g) was added to a dichloromethane (20 ml) solution of 2-(4-trifluoromethoxyphenoxy)ethylamine (1.10 g) and 2,4,6-trifluorobenzoic acid (0.87 g) and the mixture was stirred at room temperature for 3 hours.

After completion of the reaction, water (10 ml) was added to the reaction mixture and extraction was carried out. The organic layer was washed with a saturated saline solution and dried over anhydrous sodium sulfate, and then the solvent was removed under reduced pressure.

The resulting residue was purified by silica gel chromatography (Wako gel C-200, eluted by toluene:ethyl acetate= 9:1) to obtain 1.27 g of the title compound as colorless crystal.

$^1$H-NMR (CDCl$_3$, δ ppm)

3.77 to 4.23 (4H, m), 6.26 to 6.48 (1H, br), 6.61 to 7.26 (6H, m)

(5) Synthesis of N-[2-(4-trifluoromethoxyphenoxy)ethyl]-2-methylbenzamide (Compound (1-15))

A tetrahydrofuran (5 ml) solution of 2-methylbenzoyl chloride (0.77 g) was added dropwise under ice-cooling and stirring to a tetrahydrofuran (20 ml) solution of 2-(4-trifluoromethoxyphenoxy)ethylamine (1.10 g) and triethylamine (0.51 g) and the mixture was further stirred at room temperature for one hour.

After completion of the reaction, the resulting triethylamine hydrochloride was removed by filtration, and then the solvent was removed under reduced pressure.

The resulting residue was purified by silica gel chromatography (Wako gel C-200, eluted by toluene:ethyl acetate= 9:1) to obtain 1.31 g of the title compound as colorless crystal.

(6) Synthesis of N-[2-(4-trifluoromethoxyphenoxy)ethyl]-2-trifluoromethylbenzoylamide (Compound (1-17))

A tetrahydrofuran (5 ml) solution of 2-trifluoromethylbenzoyl chloride (1.04 g) was added dropwise under ice-cooling and stirring to a tetrahydrofuran (20 ml) solution of 2-(4-trifluoromethoxyphenoxy)ethylamine (1.10 g) and triethylamine (0.51 g) and the mixture was further stirred at room temperature for one hour.

After completion of the reaction, the formed triethylamine hydrochloride was removed by filtration, and the solvent was removed under reduced pressure.

The resulting residue was purified by silica gel chromatography (Wako gel C-200, eluted by toluene:ethyl acetate= 9:1) to obtain 1.67 g of the title compound as colorless crystal.

$^1$H-NMR (CDCl$_3$, δ ppm)

3.79 to 4.18 (4H, m), 6.15 to 6.31 (1H, br), 6.80 to 7.76 (8H, m)

(7) Synthesis of N-[2-(4-difluoromethoxyphenoxy)ethyl]-2,6-difluorobenzamide (Compound (1-35))

To a mixed solution of dichloromethane (30 ml) and water (10 ml) were added N-[2-(4-hydroxyphenoxy)ethyl]-2,6-difluorobenzamide (1.16 g), potassium hydroxide (1.10 g) and tetrabutylammonium bromide (0.10 g), then chlorodifluoromethane (3.50 g) was slowly blown therein at room temperature under stirring, and the mixture was further stirred at room temperature for one hour.

After completion of the reaction, dichloromethane was added to the reaction mixture to extract the title compound. The organic layer was washed with a saturated saline solution and dried over anhydrous sodium sulfate, and then the solvent was removed under reduced pressure.

The resulting residue was purified by silica gel chromatography (wako gel C-200, eluted by toluene:ethyl acetate= 9:1) to obtain 0.87 g of the title compound as colorless crystal.

$^1$H-NMR (CDCl$_3$, δ ppm)

3.78 to 4.20 (4H, m), 6.42 (1H, t, J=74.2), 6.28 to 6.51 (1H, br), 6.71 to 7.44 (7H, m)

(8) Synthesis of N-{2-[4-(2-chloro-1,1,2-trifluoroethoxy)-phenoxy]ethyl}-2,6-difluorobenzamide (Compound (1-38))

A tetrahydrofuran (5 ml) solution of 2,6-difluorobenzoyl chloride (0.71 g) was added dropwise under ice-cooling and stirring to a tetrahydrofuran (20 ml) solution of 2-[4-(2-chloro-1,1,2-trifluoroethoxy)phenoxy]ethylamine (1.08 g) and triethylamine (0.40 g) and the mixture was further stirred at room temperature for one hour.

After completion of the reaction, the formed triethylamine hydrochloride was removed by filtration, and the solvent was removed under reduced pressure.

The resulting residue was purified by silica gel chromatography (Wako gel C-200, eluted by toluene:ethyl acetate= 9:1) to obtain 1.76 g of the title compound as colorless crystal.

$^1$H-NMR (CDCl$_3$, δ ppm)

3.77 to 4.21 (4H, m), 6.14 to 6.35 (1H, m), 6.53 to 6.73 (1H, br), 6.73 to 7.44 (7H, m)

(9) Synthesis of N-{2-[4-(2,2,2-trifluoroethoxy)phenoxy]ethyl}-2,6-difluorobenzamide (Compound (1-40))

A tetrahydrofuran (5 ml) solution of 2,6-difluorobenzoyl chloride (0.70 g) was added dropwise under ice-cooling and stirring to a tetrahydrofuran (20 ml) solution of 2-[4-(2,2,2-trifluoroethoxy)phenoxy]ethylamine (0.94 g) and triethylamine (0.40 g) and the mixture was further stirred at room temperature for one hour.

After completion of the reaction, the formed triethylamine hydrochloride was removed by filtration, and the solvent was removed under reduced pressure.

The resulting residue was purified by silica gel chromatography (Wako gel C-200, eluted by toluene:ethyl acetate= 9:1) to obtain 1.18 g of the title compound as colorless crystal.

$^1$H-NMR (CDCl$_3$, δ ppm)

3.80 to 4.40 (6H, m), 6.28 to 6.53 (1H, br), 6.72 to 7.44 (1H, m)

(10) Synthesis of N-[3-(4-trifluoromethoxyphenoxy)propyl]-2,6-difluorobenzamide (Compound (1-43))

A tetrahydrofuran (5 ml) solution of 2,6-difluorobenzoyl chloride (0.88 g) was added dropwise under ice-cooling and stirring to a tetrahydrofuran (20 ml) solution of 3-(4-trifluoromethoxyphenoxy)propylamine (1.18 g) and triethylamine (0.50 g) and the mixture was further stirred at room temperature for one hour.

After completion of the reaction, the formed triethylamine hydrochloride was removed by filtration, and the solvent was removed under reduced pressure.

The resulting residue was purified by silica gel chromatography (Wako gel C-200, eluted by toluene:ethyl acetate= 9:1) to obtain 1.38 g of the title compound as colorless crystal.

$^1$H-NMR (CDCl$_3$, δ ppm)

2.03 to 2.21 (4H, m), 3.57 to 4.14 (4H, m), 6.19 to 6.38 (1H, br), 6.74 to 7.43 (7H, m)

(11) Synthesis of N-[2-(4-trifluoromethoxyphenoxy)ethyl]-2,6-difluorobenzthioamide (Compound (1-2))

Lawesson's reagent (1.94 g) was added to a toluene (20 ml) solution of N-[2-(4-trifluoromethoxyphenoxy)ethyl]-2,6-difluorobenzamide (1.44 g) and the mixture was stirred at room temperature for 3 hours.

After completion of the reaction, the solvent was removed under reduced pressure.

The resulting residue was purified by silica gel chromatography (Wako gel C-200, eluted by toluene:ethyl acetate= 20:1) to obtain 1.56 g of the title compound as a pale yellowish crystal.

$^1$H-NMR (CDCl$_3$, δ ppm)

4.20 to 4.37 (4H, m), 6.79 to 7.38 (7H, m), 7.71 to 7.89 (1H, br)

(12) Synthesis of other Compound (1) in Table 3

In accordance with the methods described in the above-mentioned (1) to (11), the other Compounds (1) in Table 3 was synthesized.

The thus synthesized (1) to (11) as mentioned above and physical properties thereof are shown in Table 3.

TABLE 3

$$R^3 \underset{R^2}{\overset{R^1}{\bigcirc}} \overset{A}{\underset{\|}{C}} - NH-(CH_2)_n-O-\bigcirc-OC_xH_yF_zCl_m$$

| Compound | $R^1$ | $R^2$ | $R^3$ | $OC_xH_yF_zCl_m$ | A | n | Physical properties |
|---|---|---|---|---|---|---|---|
| 1-1 | H | H | H | 4-$OCF_3$ | O | 2 | m.p. 93~95° C. |
| 1-2 | F | H | H | 4-$OCF_3$ | O | 2 | m.p. 57~58° C. |
| 1-3 | Cl | H | H | 4-$OCF_3$ | O | 2 | m.p. 68~70° C. |
| 1-4 | Br | H | H | 4-$OCF_3$ | O | 2 | m.p. 82~84° C. |
| 1-5 | H | H | 3-F | 4-$OCF_3$ | O | 2 | |
| 1-6 | H | H | 3-Cl | 4-$OCF_3$ | O | 2 | |
| 1-7 | H | H | 4-F | 4-$OCF_3$ | O | 2 | |
| 1-8 | H | H | 4-Cl | 4-$OCF_3$ | O | 2 | m.p. 108~110° C. |
| 1-9 | H | H | 4-Br | 4-$OCF_3$ | O | 2 | |
| 1-10 | F | H | H | 4-$OCF_3$ | O | 2 | m.p. 79~81° C. |
| 1-11 | F | Cl | H | 4-$OCF_3$ | O | 2 | m.p. 104~105° C. |
| 1-12 | Cl | Cl | H | 4-$OCF_3$ | O | 2 | m.p. 133~134° C. |
| 1-13 | F | H | 4-F | 4-$OCF_3$ | O | 2 | m.p. 66~67° C. |
| 1-14 | F | F | 4-F | 4-$OCF_3$ | O | 2 | m.p. 113~114° C. |
| 1-15 | $CH_3$ | H | H | 4-$OCF_3$ | O | 2 | m.p. 56~58° C. |
| 1-16 | $CH_3O$ | H | H | 4-$OCF_3$ | O | 2 | $n_D^{20}$ 1.5260 |
| 1-17 | $CF_3$ | H | H | 4-$OCF_3$ | O | 2 | m.p. 72~74° C. |
| 1-18 | $CHF_2O$ | H | H | 4-$OCF_3$ | O | 2 | |
| 1-19 | $CF_3O$ | H | H | 4-$OCF_3$ | O | 2 | m.p. 69~70° C. |
| 1-20 | $CF_3$ | H | H | 4-$OCF_3$ | O | 2 | m.p. 108~110° C. |
| 1-21 | H | H | 3-$CH_3$ | 4-$OCF_3$ | O | 2 | |
| 1-22 | H | H | 3-$CH_3O$ | 4-$OCF_3$ | O | 2 | |
| 1-23 | H | H | 3-$CF_3$ | 4-$OCF_3$ | O | 2 | |
| 1-24 | H | H | 3-$CF_3O$ | 4-$OCF_3$ | O | 2 | |
| 1-25 | H | H | 4-$CH_3$ | 4-$OCF_3$ | O | 2 | |
| 1-26 | H | H | 4-$CH_3O$ | 4-$OCF_3$ | O | 2 | |
| 1-27 | H | H | 4-$CF_3$ | 4-$OCF_3$ | O | 2 | m.p. 101~104° C. |
| 1-28 | H | H | 4-$CF_3O$ | 4-$OCF_3$ | O | 2 | m.p. 74~76° C. |
| 1-29 | CN | H | H | 4-$OCF_3$ | O | 2 | m.p. 95~98° C. |
| 1-30 | $NO_2$ | H | H | 4-$OCF_3$ | O | 2 | m.p. 99~100° C. |
| 1-31 | H | H | 3-CN | 4-$OCF_3$ | O | 2 | m.p. 76~77° C. |
| 1-32 | H | H | 3-$NO_2$ | 4-$OCF_3$ | O | 2 | |
| 1-33 | H | H | 4-CN | 4-$OCF_3$ | O | 2 | |
| 1-34 | H | H | 4-$NO_2$ | 4-$OCF_3$ | O | 2 | m.p. 123~125° C. |
| 1-35 | F | F | H | 4-$OCHF_2$ | Q | 2 | m.p. 86~89° C. |
| 1-36 | F | F | H | 4-$OCF_2CFH_2$ | O | 2 | |
| 1-37 | F | F | H | 4-$OCF_2CF_2H$ | O | 2 | m.p. 98~100° C. |
| 1-38 | F | F | H | 4-$OCF_2CFClH$ | O | 2 | m.p. 82~84° C. |
| 1-39 | F | F | H | 4-$OCF_2CFHCF_3$ | O | 2 | |
| 1-40 | F | F | H | 4-$OCH_2CF_3$ | O | 2 | m.p.122~124° C. |
| 1-41 | F | F | H | 2-$OCF_3$ | O | 2 | |
| 1-42 | F | F | H | 3-$OCF_3$ | O | 2 | m.p. 65~67° C. |
| 1-43 | F | F | H | 4-$OCF_3$ | O | 3 | m.p. 108~109° C. |
| 1-44 | F | F | H | 4-$OCF_3$ | O | 5 | |
| 1-45 | F | F | H | 4-$OCHF_2$ | S | 2 | |
| 1-46 | F | F | H | 4-$OCF_3$ | S | 2 | m.p. 64~65° C. |
| 1-47 | F | F | H | 4-$OCF_2CFH_2$ | S | 2 | |
| 1-48 | F | F | H | 4-$OCF_2CF_2H$ | S | 2 | |
| 1-49 | F | F | H | 4-$OCF_2CFClH$ | S | 2 | |
| 1-50 | F | F | H | 4-$OCF_2CFHCF_3$ | S | 2 | |
| 1-51 | F | F | H | 4-$OCH_2CF_3$ | S | 2 | |
| 1-52 | $CH_3$ | $CH_3$ | H | 4-$OCF_3$ | O | 2 | m.p.122~123° C. |
| 1-53 | $CH_3O$ | $CH_3O$ | H | 4-$OCF_3$ | O | 2 | m.p.112~113° C. |
| 1-54 | $CH_3$ | Cl | H | 4-$OCF_3$ | O | 2 | |
| 1-55 | OH | H | H | 4-$OCF_3$ | O | 2 | m.p.103~105° C. |
| 1-56 | OH | H | 4-Cl | 4-$OCF_3$ | O | 2 | m.p. 101~102° C. |

(m.p.: melting point)

Example 3

(Preparation of Formulation)

(1) Preparation of Granule

Five parts by weight of Compound (1-1), 35 parts by weight of bentonite, 57 parts by weight of talc, 1 part by weight of Neopelex powder (trade name, produced by Kao K.K.) and 2 parts by weight of sodium lignosulfonate were uniformly mixed, and then, the mixture was kneaded with addition of a small amount of water, followed by granulation and drying, to obtain a granule.

(2) Preparation of Wettable Powder

Ten parts by weight of Compound (1-1), 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.) were uniformly mixed, and then the mixture was pulverized to obtain a wettable powder.

(3) Preparation of Emulsifiable Concentrate

Twenty parts by weight of Compound (1-1), 70 parts by weight of xylene by adding 10 parts by weight of Toxanone (trade name, produced by Sanyo Kasei Kogyo) were uniformly mixed, and dissolved therein to obtain an emulsifiable concentrate.

(4) Preparation of Dustable Powder

Five parts by weight of Compound (1-1), 50 parts by weight of talc and 45 parts by weight of kaolin were uniformly mixed to obtain a dustable powder.

Example 4

(Tests of Effects)

(1) Test of Effect on Southern Root-knot Nematode

The respective wettable powders of the compounds (1) shown in Table 3 prepared in accordance with Example 3 were diluted to 300 ppm with water and 0.1 ml thereof was placed in a test tube, and 0.9 ml of an aqueous solution containing about 500 southern root-knot nematodes was placed therein (final concentration: 30 ppm).

Next, these test tubes were left to stand in a thermostat chamber at 25° C., and after 2 days, nematocidal rate was determined by observing with a microscope.

The nematocidal effect was evaluated by using 4 ranks of A to D depending on the range of nematocidal rate (A: 100%, B: less than 100 to 80%, C: less than 80 to 60% and D: less than 60%). These results are shown in Table 4.

TABLE 4

Test of effect on southern root-knot nematode

| Compound | Effect |
| --- | --- |
| 1-2 | A |
| 1-3 | A |
| 1-10 | A |
| 1-14 | A |
| 1-15 | A |
| 1-16 | A |
| 1-17 | A |
| 1-30 | A |
| 1-35 | A |
| 1-37 | A |
| 1-38 | A |
| 1-40 | A |
| 1-43 | A |
| 1-46 | A |

(2) Test of Effect on Two-spotted Spider Mite Egg

The respective wettable powders of the compounds (1) shown in Table 3 prepared in accordance with Example 3 were diluted to 300 ppm with water containing a surfactant (0.01%), and in these respective chemical solutions, kidney bean leaves (diameter: 20 mm) on which 15 two-spotted spider mite female adults were infested for 24 hours to lay eggs and then eliminated were dipped for 10 seconds, respectively.

Next, test tubes in which each of these leaves were placed were left to stand in a thermostat chamber at 25° C., and after 6 days, egg killing rate was determined by counting unhatched larvae in the respective leaves.

The evaluation of the egg killing effect was shown by 4 ranks of A to D depending on the range of egg killing rate (A: 100%, B: less than 100 to 80%, C: less than 80 to 60% and D: less than 60%).

These results of evaluating these egg killing effects are shown in Table 5.

TABLE 5

Test of effect on two-spotted spider mite egg

| Compound | Effect |
| --- | --- |
| 1-2 | A |
| 1-4 | A |
| 1-13 | A |
| 1-19 | A |
| 1-30 | A |
| 1-35 | A |
| 1-46 | A |

(3) Test of controlling effect on rice blast (preventive effect)

In plastic flowerpots having a diameter of 6 cm, 10 rices (seedlings variety: Nihonbare) were grown per one flowerpot, and to the young plants at 1.5 leaf stage, the chemicals obtained by diluting the wettable powder of the compounds (1) shown in Table 3 prepared in accordance with Example 3 to 500 ppm with water containing a surfactant (0.01%) were sprayed in an amount of 20 ml per one flowerpot, respectively.

After spraying, the rice seedlings were grown in a glass greenhouse for 2 days, and then a suspension of conidiospores of rice blast collected from infected leaves was sprayed uniformly to the plant leaves to be inoculated thereinto.

After inoculation, the rice seedlings were grown in a moist chamber at 28° C. for 5 days, and the degree of lesion of rice blast appeared on the leaves was examined.

The fungicidal effect was evaluated by using 6 ranks of 0 to 5 as compared with the degree of lesion in the non-treated control (0: all area is infected, 1: lesion area is about 60%, 2: lesion area is about 40%, 3: lesion area is about 20%, 4: lesion area is 10% or less and 5: no lesion is observed).

The results are shown in Table 6.

TABLE 6

Test of controlling effect on rice blast (preventive effect)

| Compound | Effects |
| --- | --- |
| 1-1 | 3 |
| 1-2 | 1 |
| 1-8 | 4 |
| 1-10 | 1 |
| 1-13 | 1 |
| 1-19 | 2 |
| 1-46 | 2 |
| 1-55 | 2 |
| 1-56 | 4 |
| Non-treated district | 0 |

(4) Test of controlling effect on wheat brown rust (preventive effect)

In plastic flowerpots having a diameter of 6 cm, 10 wheat seedlings (variety: Kobushi Komugi) were grown per one flowerpot, and to the young plants at 1.5 leaf stage, the chemicals obtained by diluting the wettable powders of the compounds (1) shown in Table 3 prepared in accordance with Example 3 to 500 ppm with water containing a surfactant (0.01%) were sprayed in an amount of 20 ml per one flowerpot, respectively.

After spraying, the wheat seedlings were grown in a glass greenhouse for 2 days, and then a suspension of spores of wheat brown rust ($3 \times 10^5$ spores/ml) was sprayed uniformly to the plants to be inoculated thereinto.

After inoculation, the wheat seedlings were grown in a glass greenhouse for one week, and the degree of lesion of wheat brown rust appeared on the first leaves was examined.

The results are shown in Table 7 according to the 6 rank evaluation method described in the above (3).

TABLE 7

Test of controlling effect on wheat brown rust (preventive effect)

| Compound | Effects |
|---|---|
| 1-1 | 4 |
| 1-2 | 3 |
| 1-8 | 3 |
| 1-10 | 1 |
| 1-13 | 1 |
| 1-19 | 2 |
| 1-30 | 3 |
| 1-46 | 1 |
| 1-52 | 2 |
| 1-53 | 4 |
| 1-55 | 3 |
| 1-56 | 2 |
| Non-treated district | 0 |

Utilizability in Industry

The novel N-[(fluoroalkoxy)phenoxyalkyl]benzamide derivative of the present invention has excellent effects of nematocidal, acaricidal, fungicidal, etc.

We claim:

1. An N-[(fluoroalkoxy)phenoxyalkyl]benzamide compound represented by the formula (1):

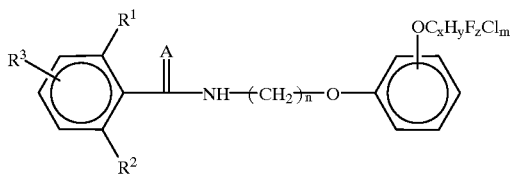

(1)

wherein $R^1$ represents a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group, a nitro group, or a hydroxy group;

$R^2$ represents a hydrogen atom, a halogen atom, an alkyl group having 1 to 4 carbon atom, or an alkoxy group having 1 to 4 carbon atom;

$R^3$ represents a hydrogen atom, a halogen atom, an alkyl group having 1 to 4 carbon atoms, an alkoxy group having 1 to 4 carbon atoms, a haloalkyl group having 1 to 4 carbon atoms, a haloalkoxy group having 1 to 4 carbon atoms, a cyano group, or a nitro group;

A represents an oxygen atom, or a sulfur atom;

n represents an integer of 1 to 6;

x represents an integer of 1 to 4;

y represents an integer of 0 to 6;

z represents an integer of 2 to 9;

m represents an integer of 0 to 2;

provided that $2x+1=y+z+m$.

2. The compound according to claim 1, wherein $R^1$ is a hydrogen atom, a fluorine atom, a chlorine atom, a bromine atom, a methyl group, a methoxy group, $CF_3$, $CHF_2O$ or $CF_3O$.

3. The compound according to claim 1, wherein $R^2$ is a hydrogen atom, a fluorine atom, a methyl group or a methoxy group.

4. The compound according to claim 1, wherein $R^3$ is a hydrogen atom, a chlorine atom, an iodine atom, a bromine atom, a fluorine atom, $CF_3$ or $CF_3O$, and substituted at 4-position.

5. The compound according to claim 1, wherein the compound of the formula (1) is one selected from the group consisting of the following (a) to (s):

(a) Compound (1) in which $R^1$ to $R^3$ are hydrogen atoms, $OC_xH_yF_zCl_m$ is 3-$OC_xF_z$ or 4-$OC_xF_z$, A is an oxygen atom and n is 2;

(b) Compound (1) in which $R^1$ is a hydrogen atom, $R^2$ and $R^3$ are hydrogen atoms, $OC_xH_yF_zCl_m$ is 3-$OC_xF_z$ or 4-$OC_xF_z$, A is an oxygen atom and n is 2;

(c) Compound (1) in which $R^1$ and $R^2$ are hydrogen atoms, $R^3$ is a halogen atom, $OC_xH_yF_zCl_m$ is 3-$OC_xF_z$ or 4-$OC_xF_z$, A is an oxygen atom and n is 2;

(d) Compound (1) in which $R^1$ and $R^2$ are halogen atoms, $R^3$ is a hydrogen atom, $OC_xH_yF_zCl_m$ is 3-$OC_xF_z$ or 4-$OC_xF_z$, A is an oxygen atom and n is 2;

(e) Compound (1) in which $R^1$ and $R^3$ are halogen atoms, $R^2$ is a hydrogen atom, $OC_xH_yF_zCl_m$ is 3-$OC_xF_z$ or 4-$OC_xF_z$, A is an oxygen atom and n is 2;

(f) Compound (1) in which $R^1$ to $R^3$ are halogen atoms, $OC_xH_yF_zCl_m$ is 3-$OC_xF_z$ or 4-$OC_xF_z$, A is an oxygen atom and n is 2;

(g) Compound (1) in which $R^1$ is an alkyl group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2;

(h) Compound (1) in which $R^1$ is an alkoxy group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2;

(i) Compound (1) in which $R^1$ is a haloalkyl group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2;

(j) Compound (1) in which $R^1$ and $R^2$ are halogen atoms, $R^3$ is a hydrogen atom, $OC_xH_yF_zCl_m$ is 4-$OC_xH_yF_z$, A is an oxygen atom and n is 2;

(k) Compound (1) in which $R^1$ and $R^2$ are halogen atoms, $R^3$ is a hydrogen atom, $OC_xH_yF_zCl_m$ is 4-$OC_xH_yF_zCl_m$, A is an oxygen atom and n is 2;

(l) Compound (1) in which $R^1$ and $R^2$ are halogen atoms, $R^3$ is a hydrogen atom, $OC_xH_yF_zCl_m$ is 3-$OC_xF_z$ or 4-$OC_xF_z$, A is a sulfur atom and n is 2;

(m) Compound (1) in which $R^1$ is a haloalkoxy group having 1 to 4 carbon atoms, $R^2$ and $R^3$ are hydrogen atoms, $OC_xH_yF_zCl_m$ is 3-$OC_xF_z$ or 4-$OC_xF_z$, A is an oxygen atom and n is 2;

(n) Compound (1) in which $R^1$ is a nitro group, $R^2$ and $R^3$ are hydrogen atoms, $OC_xH_yF_zCl_m$ is 3-$OC_xF_z$ or 4-$OC_xF_z$, A is an oxygen atom and n is 2;

(o) Compound (1) in which $R^1$ and $R^2$ are an alkyl group having 1 to 4 carbon atoms, $R^3$ is a hydrogen atom, $OC_xH_yF_zCl_m$ is 3-$OC_xF_z$ or 4-$OC_xF_z$, A is an oxygen atom and n is 2;

(p) Compound (1) in which $R^1$ and $R^2$ are an alkoxy group having 1 to 4 carbon atoms, $R^3$ is a hydrogen atom, $OC_xH_yF_zCl_m$ is 3-$OC_xF_z$ or 4-$OC_xF_z$, A is an oxygen atom and n is 2;

(q) Compound (1) in which $R^1$ is a hydroxyl group, $R^2$ and $R^3$ are hydrogen atoms, $OC_xH_yF_zCl_m$ is 3-$OC_xF_z$ or 4-$OC_xF_z$, A is an oxygen atom and n is 2;

(r) Compound (1) in which $R^1$ is a hydroxyl group, $R^2$ is a hydrogen atom, $R^3$ is a halogen atom, $OC_xH_yF_zCl_m$ is 3-$OC_xF_z$ or 4-$OC_xF_z$, A is an oxygen atom and n is 2; and (s) Compound (1) in which $R^1$ and $R^3$ are halogen atoms, $R^2$ is a hydrogen atom, $OC_xH_yF_zCl_m$ is 3-$OC_xH_yF_zCl_m$ or 4-$OC_xF_z$, A is an oxygen atom and n is 3.

6. The compound according to claim 1, wherein the compound of the formula (1) is one selected from the group consisting of the following (1) to (11):

(1) N-[2-(4-trifluoromethoxyphenoxy)ethyl]-2-fluorobenzamide (Compound (1-2));
(2) N-[2-(4-trifluoromethoxyphenoxy)ethyl]-2-chlorobenzamide (Compound (1-3));
(3) N-[2-(4-trifluoromethoxyphenoxy)ethyl]-2,6-difluorobenzamide (Compound (1-10));
(4) N-[2-(4-trifluoromethoxyphenoxy)ethyl]-2,4,6-trifluorobenzamide (Compound (1-14));
(5) N-[2-(4-trifluoromethoxyphenoxy)ethyl]-2-methylbenzamide (Compound (1-15));
(6) N-[2-(4-trifluoromethoxyphenoxy)ethyl]-2-trifluoromethylbenzoylamide (Compound (1-17));
(7) N-[2-(4-difluoromethoxyphenoxy)ethyl]-2,6-difluorobenzamide (Compound (1-35));
(8) N-{2-[4-(2-chloro-1,1,2-trifluoroethoxy)phenoxy]ethyl}-2,6-difluorobenzamide (Compound (1-38));
(9) N-{2-[4-(2,2,2-trifluoroethoxy)phenoxy]ethyl}-2,6-difluorobenzamide (Compound (1-40));
(10) N-[3-(4-trifluoromethoxyphenoxy)propyl]-2,6-difluorobenzamide (Compound (1-43)); and
(11) N-[2-(4-trifluoromethoxyphenoxy)ethyl]-2,6-difluorobenzthioamide (Compound (1-2)).

7. A process for preparing the N-[(fluoroalkoxy)phenoxyalkyl]benzamide derivative in which A represents an oxygen atom in the formula (1) according to claim 1, which comprises reacting a (fluoroalkoxy)phenoxyalkylamine compound represented by the following formula (2):

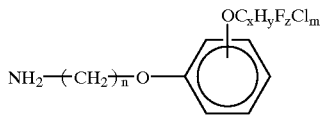

(2)

wherein n, x, y, z and m have the same meanings as defined in claim 1, and a carboxylic acid compound represented by the following formula (3):

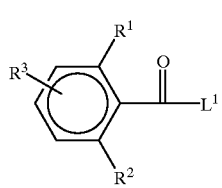

(3)

wherein $R^1$ to $R^3$ have the same meanings as defined claim 1; and $L^1$ represents a halogen atom, or a hydroxy group.

8. The process according to claim 7, wherein $L^1$ is a halogen atom, and the reaction is carried out in a solvent or without a solvent in the presence of a base at 0 to 30° C. for 0.1 to 2 hours.

9. The process according to claim 7, wherein Compound (3) is used in a ratio of 0.5 to 2 moles based on 1 mole of Compound (2) and a base is used in an amount of 1 to 10-fold moles based on Compound (2).

10. The process according to claim 7, wherein $L^1$ is a hydroxyl group, and the reaction is carried out in a solvent or without a solvent in the presence of a condensing agent at 0 to 50° C. for 0.5 to 8 hours.

11. The process according to claim 7, wherein Compound (3) is used in a ratio of 0.5 to 2 moles based on 1 mole of Compound (2) and a condensing agent is used in an amount of 1 to 10-fold moles based on Compound (2).

12. A (fluoroalkoxy)phenoxyalkylamine compound represented by the following formula (2):

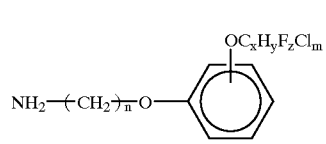

(2)

wherein n, x, y, z and m have the same meanings as defined in claim 1.

13. The compound according to claim 12, wherein the compound of the formula (2) is one selected from the group consisting of the following (1) to (6):

(1) 2-(4-trifluoromethoxyphenoxy)ethylamine (Compound (2-2));
(2) 2-[4-(2,2,2-trifluoroethoxy)phenoxy]ethylamine (Compound (2-3));
(3) 2-[4-(1,1,2,2-tetrafluoroethoxy)phenoxy]ethylamine (Compound (2-5));
(4) 2-[4-(2-chloro-1,1,2-trifluoroethoxy)phenoxy]ethylamine (Compound (2-6));
(5) 2-(3-trifluoromethoxyphenoxy)ethylamine (Compound (2-9)); and
(6) 3-(4-trifluoromethoxyphenoxy)propylamine (Compound (2-10)).

14. A process for preparing the (fluoroalkoxy)phenoxyalkylamine compound represented by the above formula (2) according to claim 12, which comprises subjecting a (fluoroalkoxy)phenoxyalkyl compound represented by the following formula (4):

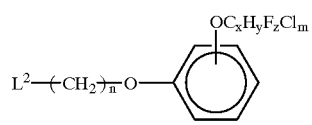

(4)

wherein $L^2$ represents a halogen atom, a methanesulfonyloxy group, or a toluenesulfonyloxy group; n, x, y, z and m have the same meanings as defined in claim 1, to amination.

15. An agricultural and horticultural chemical for controlling noxious organisms containing the N-[(fluoro-alkoxy)phenoxyalkyl]benzamide compound represented by the above formula (1) according to claim 1 as an effective ingredient.

16. An agricultural and horticultural chemical for controlling noxious organisms containing the N-[(fluoroalkoxy)phenoxyalkyl]benzamide compound represented by the above formula (1) according to claim 1 as an effective ingredient and formulating at least one selected from a carrier, a surfactant, a dispersant and an auxiliary and used by formulating in the form of dust powder, an emulsifiable concentrate, a fine granule, a granule, a wettable powder, an oily suspension or an aerosol.

* * * * *